(12) United States Patent
Holzmuller et al.

(10) Patent No.: US 9,201,070 B2
(45) Date of Patent: Dec. 1, 2015

(54) ANTIGENIC STRUCTURE AND USES THEREOF FOR SCREENING TRYPANOSOMIASES IN HUMANS AND ANIMALS

(75) Inventors: Philippe Holzmuller, Poussan (FR); Silla Semballa, Bangul (CF); Philippe Vincendeau, Pessac (FR); Gerard Cuny, Castries (FR)

(73) Assignee: CENTRE DE COOPERATION INTERNATIONALE EN RECHERCHE AGRONOMIQUE POUR LE DEVELOPMENT (CIRAD), Paris (FR)

( * ) Notice: Subject to any disclaimer, the term of this patent is extended or adjusted under 35 U.S.C. 154(b) by 0 days.

(21) Appl. No.: 13/640,523

(22) PCT Filed: Apr. 13, 2011

(86) PCT No.: PCT/IB2011/051605
§ 371 (c)(1),
(2), (4) Date: Nov. 28, 2012

(87) PCT Pub. No.: WO2011/128863
PCT Pub. Date: Oct. 20, 2011

(65) Prior Publication Data
US 2013/0203085 A1 Aug. 8, 2013

(30) Foreign Application Priority Data

Apr. 13, 2010 (FR) ...................... 10 52784

(51) Int. Cl.
*G01N 33/569* (2006.01)
*C07K 14/44* (2006.01)

(52) U.S. Cl.
CPC .......... *G01N 33/56905* (2013.01); *C07K 14/44* (2013.01); *G01N 2333/44* (2013.01)

(58) Field of Classification Search
None
See application file for complete search history.

(56) References Cited

U.S. PATENT DOCUMENTS

| | | | | |
|---|---|---|---|---|
| 4,208,479 | A * | 6/1980 | Zuk et al. ...................... | 435/7.9 |
| 7,205,275 | B2 * | 4/2007 | Oliner et al. .................. | 514/7.6 |
| 2003/0224397 | A1 | 12/2003 | Lowman et al. | |

FOREIGN PATENT DOCUMENTS

| | | |
|---|---|---|
| WO | WO-97/18475 A1 | 5/1997 |
| WO | WO-03068801 A3 | 6/2005 |

OTHER PUBLICATIONS

Voller, The Enzyme Linked Immunosorbent Assay, Diagnostic Horizons, Microbiological Associates, 2(1), 1978, 1-7.*
Ball et al, A versatile synthetic peptide-based ELISA for identifying antibody epitopes, Journal of Immunological Methods 171 (1994) 37-44.*
Portsmann, Enzyme immunoassay Techniques, Journal of Immunological Methods 150 (1992) 5-21.*
Yokoyama et al., Production of Monoclonal Antibodies, In Current Protocols in Immunology, Supplement 71, (2006) 2.5.1-2.5.25.*
Chattopadhyay et al., Protein Structure and Folding: Structure of the C-terminal Domain from Trypanosoma brucei Variant Surface Glycoprotein MITat1.2, The Journal of Biological Chemistry, 2005, 280:7228-7235.*
Geffard et al., Antisera Against the Indolealkylamines: Tryptophan, 5-Hydroxytryptophan, 5-Hydroxytryptamine, 5-Methoxytryptophan, and 5-Methoxytryptamine Tested by an Enzyme-Linked Immunosorbent Assay Method, Journal of Neurochemistry, 44(4), 1985, 1221-1228.*
Reddy et al., Sequences of Three VSG mRNAs Expressed in a Mixed Population of Trypanosoma Brucei Rhodesiense, Biochemical and Biophysical Research Communications, 169(2), 730-736, 1990.*
Semballa et al., Identification of a tryptophan-like epitope borne by the variable surface glycoprotein (VSG) of African trypanosomes, Exp. Parasit., 2007, vol. 115, pp. 173-180.
Okomo-Assoumou et al., Circulating antibodies directed against tryptophan-like epitopes in sera of patients with human African trypanosomiasis, Ann. J. Trop. Med. Hyg., 1995, vol. 52, pp. 461-467.
Vincendeau et al., Importance of L-tryptophan metabolism in trypanosomiasis, Adv. Exp. Med. Biol. 1999, vol. 467, pp. 525-531.

* cited by examiner

*Primary Examiner* — Galina Yakovleva
*Assistant Examiner* — Andrea S Grossman
(74) *Attorney, Agent, or Firm* — Young & Thompson

(57) ABSTRACT

The invention relates to an antigenic structure that contains a tryptophan epitope, characterised in that said structure is made up of a tryptophan pattern W or a peptide of 3 or 4 amino acids comprising a pattern W, coupled with glutaraldehyde. The invention can he used for screening trypanosomiasis in humans or animals.

9 Claims, 4 Drawing Sheets

Figure 1A
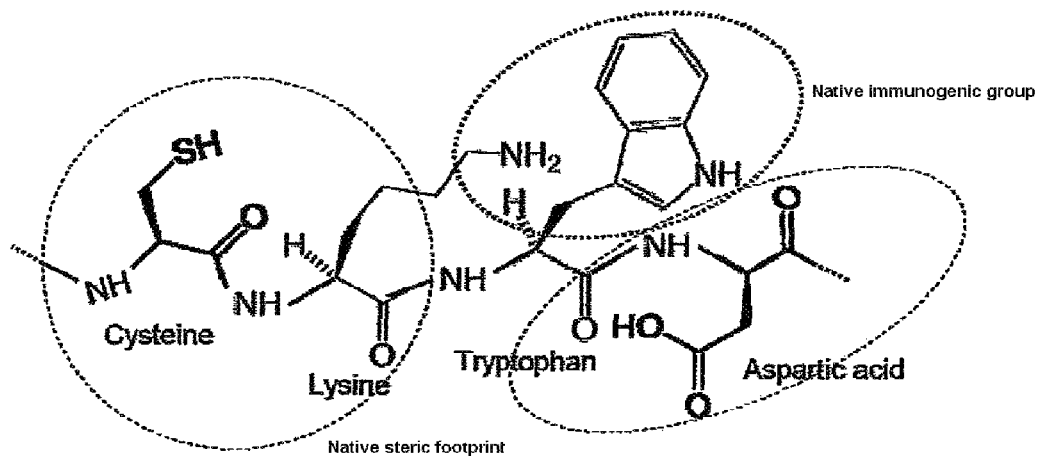
Figure 1B
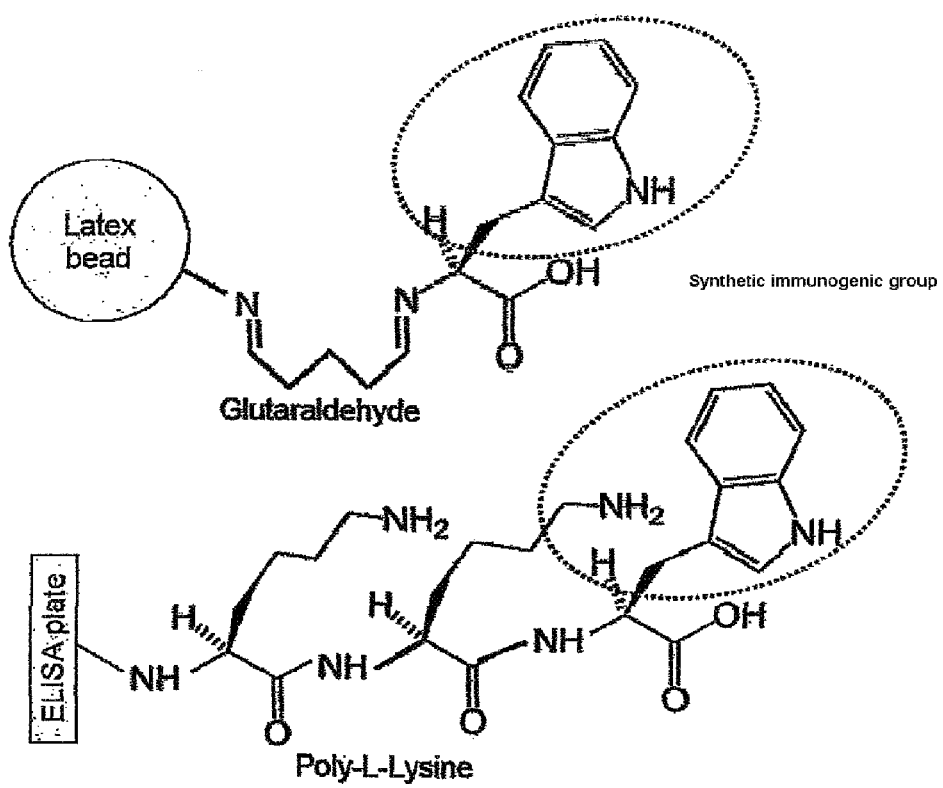
Figure 1C

Agglutination:
infected serums + WE beads

No agglutination:
healthy serums + WE beads

Agglutination:
infected blood + WE beads

No agglutination:
healthy blood + WE beads

ANTIGENIC STRUCTURE AND USES THEREOF FOR SCREENING TRYPANOSOMIASES IN HUMANS AND ANIMALS

RELATED APPLICATIONS

This application is a national stage application under 35 U.S.C. §371 of PCT/IB2011/051605, filed Apr. 13, 2011, which claims priority of French application 10/52784, filed Apr. 13, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_US_Sequence_Listing.txt. The size of the text file is 2 KB; the text file was created on Oct. 14, 2014.

The invention relates to an antigenic structure and its use for producing a kit and carrying out a method of screening for trypanosomiases in humans and animals.

Human African trypanosomiasis (HAT) and animal trypanosomiasis (AAT) mainly affect poor rural communities and are very often neglected diseases which pose a major public health problem and put a halt to the economic development of many countries. The greatest difficulty in controlling these diseases arises from the great variability of the clinical symptomatology associated with the lack of sensitivity and of specificity or with the burden of carrying out the available screening tests.

Active screening of the at-risk population is therefore essential if infected individuals are to be identified early and transmission is to be reduced by reducing the parasite reservoir. In addition, screening for HAT must include a diagnosis of stage 1 (haematolymphatic) or 2 (neurological), because patients in stage 2 are treated with melarsoprol, the toxic side-effects of which are considerable (global mortality 5-10%). Even today, stage diagnosis is based on examination of the cerebrospinal fluid after lumbar puncture, and the positivity threshold of the cerebrospinal fluid cell count is still a subject of debate (5, 10 or 20 cells/µl).

At present, the CATT (Card Agglutination Test For Trypanosomiasis)/T. b. gambiense is the most commonly used serological test. The test comprises fixed trypanosomes of the variant LiTat 1.3. A variant of the CATT is composed of semi-purified antigens (LiTat 1.3, 1.5 and 1.6) coupled to latex beads. The main problem associated with the CATT is a lack of specificity, because the antigens used are responsible for numerous cross-reactions and therefore for false positives. In addition, blood, diluted blood or plasma have variable antibody titres against these antigens. Thus, patients who are parasitologically positive may be CATT-negative. Finally, the CATT does not allow stage diagnosis and satisfactory serological monitoring of patients after treatment, in particular because of cross-reactions with other infections.

The value of having available novel antigens for improving the screening, stage determination and monitoring of HAT and AAT will therefore be appreciated. Although some antigens have been found to be valuable from a pathophysiological point of view, the handling thereof in field conditions (Semballa et al., 2004 (ref. 1)) has proved difficult.

Tryptophan-like epitopes (WE), which represent constant trypanosome antigens, induce specific antibodies in the host (human or animal). These epitopes include the amino acid L-tryptophan and are situated in constant regions of the C-terminal part of variable surface glycoproteins (VSG). High titres of anti-WE antibodies of isotype IgM have been measured by ELISA in the serum of patients affected by human African trypanosomiasis (HAT), and elevated titres have been found in patients in stage 2 (Okomo-Assoumou et al., 1995 (ref. 2)).

These pioneering results were obtained by the laboratory of the inventors by virtue of synthetic epitopes proposed for studying their recognition by anti-WE antibodies, especially WE-glutaraldehyde-BSA structures. In these structures, glutaraldehyde acts as the fixer between the synthetic antigen WE and the carrier protein (in this case bovine albumin BSA). These structures allowed the potential of the epitope WE as a diagnostic target to be demonstrated.

The work by the inventors in this field has shown an unexpected effect of glutaraldehyde relating to the optimum orientation it imparts to the synthetic antigen. It has become apparent that glutaraldehyde acts as an orientator and spacer arm for the synthetic antigen WE when it is coupled to an inert substrate such as latex beads or ELISA plates. As is shown in FIGS. 1A and 1B, to which the example below relates, the antigenic structure of the invention constitutes a mimotope of the natural antigen when it is coupled solely thereto, which permits better recognition by anti-WE antibodies.

It is, therefore, an object of the invention to provide a novel antigenic structure. The invention also aims to make use of the properties of this structure in a kit and a method of screening for human and animal trypanosomiases.

The antigenic structure of the invention is based on the coupling of an epitope of interest to glutaraldehyde and the fixing thereof to an inert substrate. The invention accordingly relates to an antigenic structure comprising a tryptophan-like epitope, characterised in that it is formed of a tryptophan unit W, or of a peptide of 3 or 4 amino acids including a unit W, coupled to glutaraldehyde.

Said peptide preferably has the amino acid sequence of SEQ ID NO: 1 or C-x-W-y, in which "x" represents K, A, S, V, T, R, I, E, D, N or G and "y" represents D, S, T, E, N, K, G, Q, R or I, it being possible for either "x" or "y" to be absent.

A representative sequence, SEQ ID NO: 2, is of the type CKWD.

According to an advantageous provision, said coupling product is grafted onto latex beads. This formulation allows the development of a rapid technique of agglutination on the serums of patients or animals affected by HAT or AAT, respectively.

According to another provision, which is advantageously used with the preceding provision, the coupling product is grafted onto ELISA plates, allowing the development of a quantitative technique for the levels of "anti-trypanosome" antibodies in patients or animals affected by HAT or AAT.

According to yet another provision, the coupling product as defined above is grafted onto poly-L-lysine deposited in the bottom of ELISA plates.

This provision allows a wholly synthetic system to be obtained, for development either in the form of beads or in the form of an ELISA test.

The invention relates also to a kit for screening for HAT or AAT, characterised in that it comprises
- at least one antigenic structure as defined above, optionally with one or more reagents for the antigen/antibody reaction and/or buffer solutions and/or reagents for the detection, quantification or visualisation of antigen/antibody complexes when they are present.

The above kit advantageously comprises, according to an additional provision of the invention, reagents for performing an immunoenzymatic revelation test, especially an indirect ELISA test or an ELISA inhibition test, in which a monoclonal anti-WE antibody is made to compete with the anti-WE antibodies of the serums of infected hosts.

In a variant embodiment, the antigenic structure is fixed to a substrate.

The invention relates further to a method of screening for HAT or AAT, characterised in that it comprises contacting of a serum sample from a patient or an animal with an antigenic structure as defined above, advantageously using a kit as described above, revelation of an immunological reaction of the antigen-antibody type.

In the variant in which the antigenic structure is fixed to latex beads, contacting with the serum sample leads to agglutination of the serum if the patient or the animal is affected by HAT or AAT, respectively.

This serological diagnostic method allows mass screening, stage determination and monitoring of HAT and AAT to be carried out. It has the advantage of being highly sensitive and highly specific, while at the same time avoiding cross-reactions with other infections (false positives) and false negatives (CATT-seronegatives in parasitology).

It will be possible to use this novel serological diagnostic test, which is inexpensive, stable and easy to carry out, where appropriate combined with an indirect ELISA test or an ELISA inhibition based on anti-WE antibodies, and which has proved its effectiveness, for mass and stage diagnosis (determination of the antibody titres of patients in stages 1 and 2) of HAT or AAT in the field, with a high degree of specificity. The test is particularly suitable for specific screening for human or animal African trypanosomiasis.

Other features and advantages of the invention are given by way of illustration in the implementation examples of the invention which follow. In these examples, reference is made to FIGS. 1 to 5, in which FIGS. 1A to 1C show the native steric footprint of the sequence CKWD (FIG. 1A), a sequence of type inert substrate with amine functional group-glutaraldehdye-W (FIG. 1B), and a sequence fixed to an ELISA plate (FIG. 1C);

EXAMPLE 1

Synthesis of W-glutaraldehyde or
C-x-W-y-glutaraldehyde Coupling Products

Production of Coupled Latex Beads

100 μl of 5% glutaraldehyde are added within a period of about 10 seconds, under a vortex, to 100 μl of haptene (tryptophan or peptide) in a concentration of 5 mg/ml in a 1.5 M acetate buffer, pH 8.3.

Without waiting, 50 μl of aminated latex beads (Sigma) are added, and the mixture is allowed to react for at least 10 minutes, with slow stirring.

The reaction is stopped by addition of 100 μl of 1M $NaBH_4$, and the mixture is stirred slowly for a further 10 minutes.

The mixture is dialysed against distilled water, to which $NaBH_4$ (1 spatula/5 l) has been added, for the whole day, the dialysis water being changed 2 to 3 times, and then for about 14 hours (overnight) with water on its own in order to remove excess $NaBH_4$.

By way of illustration, the structural chemical formulae of the native epitope sequence and of the chemical sequences used according to the invention have been given in FIGS. 1A and 1B, and they clearly show that the structure of the invention reproduces the molecular configuration of the epitope of interest.

Production of ELISA Plates

To each well of the ELISA plate (Nunc, PolySorp or MaxiSorp) there are added 200 μl of a mixture of 100 μl of haptene (tryptophan or peptide, 5 mg/ml in a 1.5 M acetate buffer, pH 8.3) and 100 μl of 5% glutaraldehyde added under a vortex within a period of about 10 seconds. The mixture is allowed to react for at least 30 minutes, with slow stirring.

The reaction is stopped by addition of 100 μl of 1M $NaBH_4$, and the mixture is stirred slowly for a further 10 minutes.

The plates are washed (5 times 1 hour) with distilled water, to which $NaBH_4$ (1 spatula/5 l) has been added, and then for about 14 hours (overnight) with water on its own in order to remove excess $NaBH_4$.

A structure with a poly-L-lysine unit fixed to an ELISA plate is given by way of illustration in FIG. 1C.

EXAMPLE 2

Diagnostic Test on Human (or Animal) Serum with Latex Beads

Figure 2:
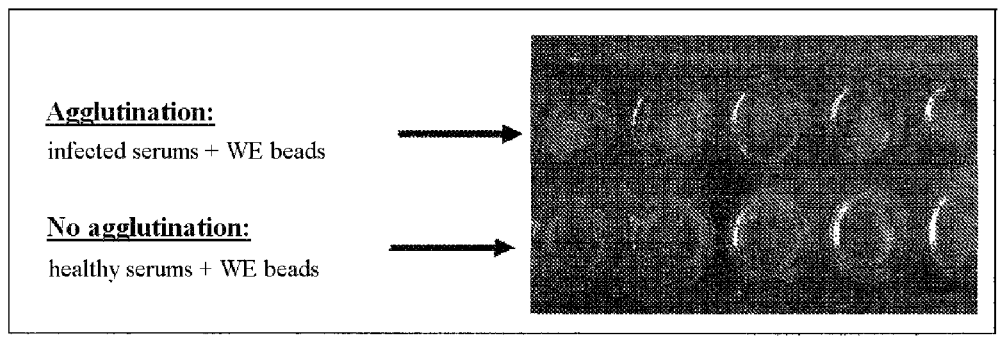
FIGS. 2 and 3 show the results of the diagnostic test on human serum and blood, respectively.
Figure 3:
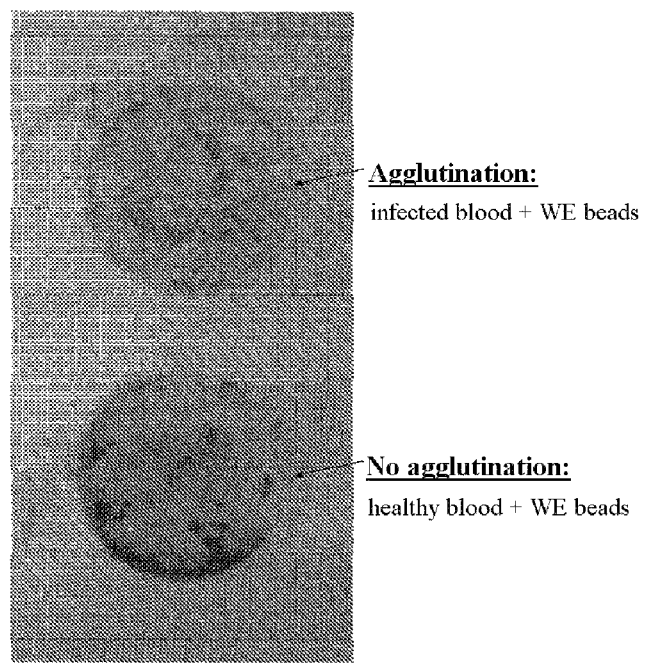
Figure 4:
FIG. 4 shows a graph of results obtained with animal serums infected by different species of Trypanosomes.

For rapid screening, 20 μl of conjugated latex beads are mixed with 20 μl of diluted or undiluted serum or 20 μl of whole blood. After 5 to 10 minutes, as shown in FIGS. 2 (with serum) and 3 (with blood), a ring characteristic of the positivity of the reaction is observed. In the absence of a ring, the reaction is considered to be negative.

EXAMPLE 3

Diagnostic Test Combining an ELISA Test for Stage Diagnosis

Figure 5:
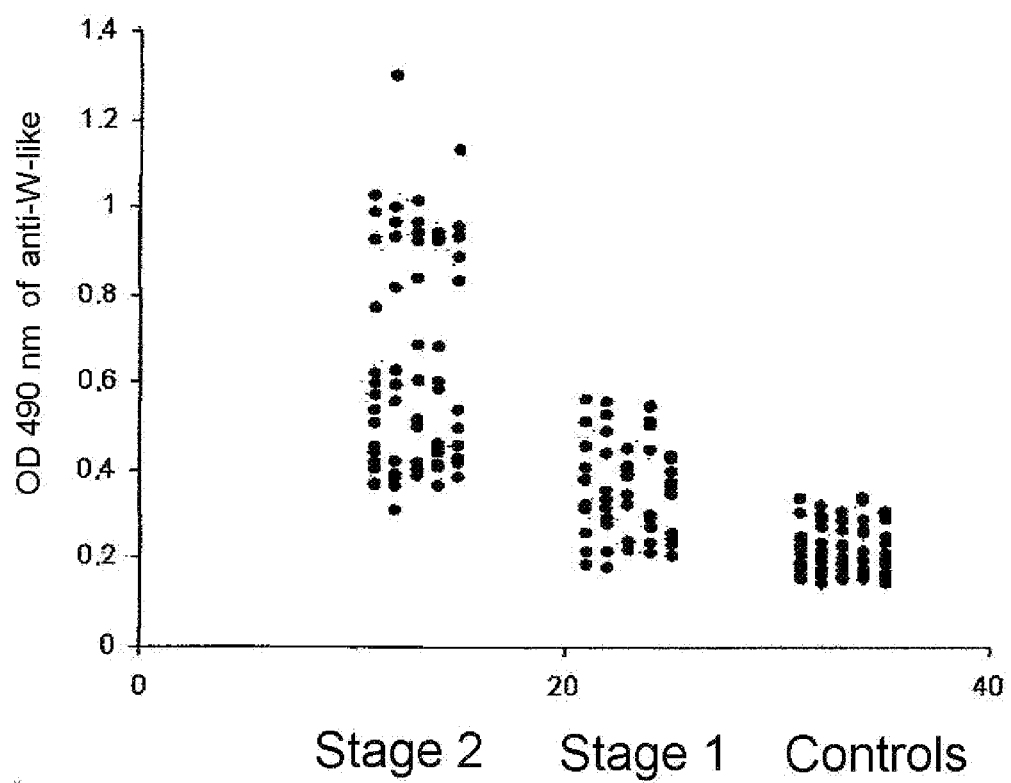
FIG. 5 shows the levels of anti-W antibodies in the serum of patients affected by HAT (stages 1 and 2).

The results obtained are shown in FIG. 5.

The use of the ELISA plates with serums of patients affected by HAT shows an increase in the levels of anti-WE antibodies on passage into stage 2 (neurological involvement).

BIBLIOGRAPHIC REFERENCES (1)—Semballa et al., experimental Parasitology 115 (2007) 173-180

(2)—Okomo-Assoumou et al., Ann. J. Trop. Med. Hyg., 1995, pp 461-467 pistage de la trypanosomose humaine ou animale

The invention claimed is:

1. An antigenic structure, consisting of a glutaraldehyde-coupling product fixed to an inert substrate, the inert substrate being latex beads or an ELISA plate, said glutaraldehyde-coupling product consisting of a peptide having the amino acid sequence CKWD (SEQ ID NO: 2) coupled to glutaraldehyde.

2. The antigenic structure of claim 1, wherein the inert substrate is latex beads.

3. The antigenic structure of claims 1, wherein the inert substrate is ELISA plates.

4. A kit for screening for human or animal trypanosomiasis, comprising the antigenic structure of claim 1 and, optionally, one or more reagents for an indirect ELISA test or an ELISA inhibition test, a buffer solution, or a reagent for detection, quantification or visualization of an antigen-antibody complex.

5. The kit of claim 4, further comprising an anti-tryptophan-like epitope antibody (anti-WE antibody) for performing an ELISA inhibition test, in which the anti-WE antibody is monoclonal and is capable of competing with an anti-WE antibody present in the serum of an infected host.

6. The kit of claim 4, which enables screening for human or animal African trypanosomiasis.

7. A method of screening for African trypanosomiasis in a human or animal subject by detecting for the presence of an antibody against a tryptophan-like epitope in a serum sample from said subject, comprising contacting the serum sample from the subject with the antigenic structure of claim 1, and detecting an immunological reaction between the antigenic structure and said antibody.

8. The method of claim 7, wherein at least one of the contacting step or the detecting step comprises contacting the serum sample or the antigenic structure with at least one of a reagent for an antigen-antibody reaction, a buffer solution, or a reagent for detection, quantification or visualisation of said immunological reaction.

9. The method of claim 7, wherein the method comprises ELISA.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = K, A, S, V, T, R, I, E, D, N or G; or Xaa
      can be absent when the amino acid in position 4 is present
<220> FEATURE:
<221> NAME/KEY: MISC_FEATURE
<222> LOCATION: (4)..(4)
<223> OTHER INFORMATION: Xaa = D, S, T, E, N, K, G, Q, R or I; or Xaa
      can be absent when the amino acid in position 2 is present

<400> SEQUENCE: 1

Cys Xaa Trp Xaa
1

<210> SEQ ID NO 2
<211> LENGTH: 4
<212> TYPE: PRT
<213> ORGANISM: Artificial sequence
<220> FEATURE:
<223> OTHER INFORMATION: Synthetic peptide

<400> SEQUENCE: 2

Cys Lys Trp Asp
1
```